(12) United States Patent
Parry et al.

(10) Patent No.: US 8,852,556 B2
(45) Date of Patent: Oct. 7, 2014

(54) ANIMAL MODEL FOR EVALUATING VASOMOTOR RESPONSE IN VIVO

(75) Inventors: Tom Jay Parry, Hellertown, PA (US); Bruce P. Damiano, Warrington, PA (US); Edward C. Giardino, Doylestown, PA (US); Margery A. Connelly, Lansdale, PA (US)

(73) Assignee: Janssen Research & Development LLC, Raritan, NJ (US)

( * ) Notice: Subject to any disclaimer, the term of this patent is extended or adjusted under 35 U.S.C. 154(b) by 740 days.

(21) Appl. No.: 12/603,360

(22) Filed: Oct. 21, 2009

(65) Prior Publication Data

US 2010/0189654 A1 Jul. 29, 2010

Related U.S. Application Data

(60) Provisional application No. 61/107,053, filed on Oct. 21, 2008.

(51) Int. Cl.
*A61K 49/00* (2006.01)

(52) U.S. Cl.
CPC .................................. *A61K 49/0008* (2013.01)
USPC .......................................................... 424/9.2

(58) Field of Classification Search
None
See application file for complete search history.

(56) References Cited

U.S. PATENT DOCUMENTS

| | | | | |
|---|---|---|---|---|
| 5,395,612 A | * | 3/1995 | Griffith et al. | ............... 424/94.6 |
| 2006/0019691 A1 | * | 1/2006 | Falotico et al. | ............... 455/518 |

FOREIGN PATENT DOCUMENTS

| | | | |
|---|---|---|---|
| EP | 0 072 061 A1 | 2/1983 | |
| JP | 2003-335674 A | 11/2003 | |
| JP | 2004-275041 A | 10/2004 | |
| WO | WO-89/04324 A1 | 5/1989 | |

OTHER PUBLICATIONS

Wadström J, Gerdin B. Modulatory effects of topically administered lidocaine and pentobarbital on traumatic vasospasm in the rabbit ear artery. 1991 Br. J. Plast. Surg. 44: 341-347.*
Drolet MC, Plante E, Battistini B, Couet J, Arsenault M. Early endothelial dysfunction in cholesterol-fed rabbits: a non-invasive in vivo ultrasound study. 2004 Cardiovasc. Ultrasound 2: 10.*
Schwarzacher S, Weidinger F, Krejcy K, Raberger G. Assessment of changes in vasomotor tone in vivo using intravascular ultrasound. 1992 J. Pharmacol. Toxicol. Methods 28: 143-147.*
Barter, P. et al., "Effects of Torcetrapib in Patients at High Risk for Coronary Events," *The New England Journal of Medicine*, 2007; 357: 2109-2122.
Chow, A. Y. et al., "Anthracyclines Cause Endothelial Injury in Pediatric Cancer Patients: A Pilot Study," *Journal of Clinical Oncology*, 2006; 24: 925-928.
Conklin, B.S. et al., "Effects of nicotine and cotinine on porcine arterial endothelial cell function," *J. Surg. Res.*, 2001; 95:23-31.
Dayal, S. et al., "Cerebral Vascular Dysfunction in Methionine Synthase-Deficient Mice," *Circulation, Journal of the American Heart Association*, 2005, 112: 737-744.
Distrutti, E. et al., "The methionine connection: homocysteine and hydrogen sulfide exert opposite effects on hepatic microcirculation in rats," *Hepatology*, 2008; 47:659-67.
El-Mas M.M. et al., Inhibition of nitric oxide-guanylate cyclase-dependent and -independent signaling contributes to impairment of beta-adrenergic vasorelaxations by cyclosporine, *Biochem Pharmacol*, 2007; 73:359-67.
Hansrani, M. et al., "The Use of an in Vivo Model to Study the Effects of Hyperhomocysteinaemia on Vascular Function," *J. Surg. Res.*, 2008; 145:13-8.
Hermann, M. et al., "Differential Effects of Selective Cyclooxygenase-2 Inhibitors on Endothelial Function in Salt-Induced Hypertension," *Circulation*, 2003; 108:2308-2311.
Higashi, Y. et al., "Excess Norepinephrine Impairs Both Endothelium-Dependent and -Independent Vasodilation in Patients With Pheochromocytoma," *Hypertension*, 2002; 39:513-518.
International Search Report, dated Feb. 11, 2010, issued in International Application No. PCT/US2009/061514 (3 pages).
Konidala, S. et al., "Coronary vasospasm and the regulation of coronary blood flow," *Prog Cardovasc Dis.* 2004; 46:349-373.
Mahmud, F.H. et al., "Impaired endothelial function in adolescents with type 1 diabetes mellitus," *J. Pediatr.*, 2008; 152:557-62.
Moat, S.J. et al., "High- but not low-dose folic acid improves endothelial function in coronary artery disease," *Eur. J. Clin. Invest.*, 2006, 36:850-9.
Mondo, C.K. et al., "Anti-oxidant effects of atorvastain in dexamethasone-induced hypertension in the rat," *Clin. Exp. Pharmacol. Physiol.*, 2006; 33:1029-34.
Sugama, D. et al., "Anti-Atherosclerotic Effects of Tamoxifen in Cholesterol-fed Ovariectomized Rabbits," *Jpn. Heart J.*, 2002, 43:545-558.
Togna, G. I. et al., "Cocaine toxic effect on endothelium-dependent vasorelaxation: an in vitro study on rabbit aorta," *Toxicology Letters*, 2001; 123:43-50.
Zhang, J.-Y. et al., "Lipid-soluble smoke particles damage endothelial cells and reduce endothelium-dependent dilatation in rat and man," *BMC Cardiovascular Disorders*, 2006; 6:3.

* cited by examiner

*Primary Examiner* — Michael G Hartley
*Assistant Examiner* — Jennifer Lamberski
(74) *Attorney, Agent, or Firm* — Bernard F. Plantz; Johnson & Johnson

(57) ABSTRACT

A method for evaluating the effect of a compound on vasomotor response in vivo comprises the steps of administering said compound to a rabbit and measuring the diameter of the vessel lumen of a central ear artery of said rabbit in comparison with the baseline diameter of the vessel lumen of said central ear artery of said rabbit, said baseline diameter being measured prior to the administration of said compound.

15 Claims, 6 Drawing Sheets

ANIMAL MODEL FOR EVALUATING VASOMOTOR RESPONSE IN VIVO

CROSS-REFERENCE TO RELATED APPLICATIONS

This application claims benefit to U.S. Provisional Patent Application No. 61/107,053, filed Oct. 21, 2008, the contents of which are incorporated by reference herein in their entirety.

BACKGROUND OF THE INVENTION

1. Field of the Invention

A method is provided for noninvasively evaluating vasoconstriction and vasodilation in vivo.

2. Description of the Related Art

The vasculature of heart, brain and kidney are capable of maintaining constant blood flow over a wide range of perfusion pressures, a phenomenon known as autoregulation. Several factors affect blood flow in the coronary and other vascular beds including arterial pressure, tissue pressure, neural and humoral influences, tissue metabolites, vascular myogenic tone, and the endothelium (reviewed by Konidala and Gutterman, 2004, Progress in Cardiovascular Diseases 46: 349-373). Appropriate vasomotor responses to constrictive and dilatory stimuli in blood vessels are key elements for regulating blood flow. Disturbances in the balance between constrictive and dilatory stimuli can affect organ blood flow (e.g. ischemia) and total peripheral resistance resulting in blood pressure changes (e.g. hypertension).

Under normal physiological conditions, resistance to blood flow may be overcome by the capability of resistance vessels to dilate in response to a number of factors. However, some pathophysiologic conditions including atherosclerosis, thrombosis and endothelial injury affect the capability of the resistance vessels to dilate in response to normal vasodilatory signals. In addition, diseases such as diabetes mellitus, obesity, congestive heart failure and hypertension, certain autoimmune disorders and certain endocrine disorders have adverse effects on dilation of resistance vessels.

Other factors such as endogenous factors, drugs, and diets may interfere with normal arterial vasodilation. For example, methionine and its metabolic byproduct homocysteine and dyslipidemia impair dilatory processes in a number of vessel types (Dayal et al., 2005, Circulation 112: 737-744; Distrutti et al., 2008, Hepatology 47: 659-667; Hansrani and Stansby, 2008, Journal of Surgical Research 145: 13-18; Moat et al., 2006, Journal of Clinical Investigation 36: 850-859). High fat or salt intake produces abnormal vasodilation (Hermann et al., 2003, Circulation 108: 2308-2311; Mahmud et al., 2008, Journal of Pediatrics 152: 557-562). Solubilized cigarette smoke particles as well as a nicotine metabolite have also been shown to block vascular relaxation (Zhang et al., 2006, BMC Cardiovascular Disorders 6:3; Conklin et al., 2001, Journal of Surgical Research, 95: 23-31). Excessive circulating norepinephrine levels, often seen in pheochromocytoma, lead to abnormalities in vasodilation (Hagashi et al., 2002, Hypertension 39: 513-518). Glucocorticoids, cocaine, certain antineoplastics, cyclosporine A, halothane, for example, are known to have adverse effect on normal arterial vasodilation (Tonga et al., 2001, Toxicology Letters 123: 43-50; El-Mas et al., 2007, Biochemical Pharmacology 73: 359-367; Chow et al., 2006, Journal of Clinical Oncology 24: 925-928; Mondo et al., 2006, Clinical and Experimental Pharmacology and Physiology 33: 1029-1034).

Studies have shown that blood vessels exhibit dilatory responses to cholinergic agonists or cholinomimetics when the endothelium is functionally intact (Sugama et al., 2002, Japan Heart J 43: 545-558; Laher et al., 1995, Canadian J Physiology Pharmacology 73: 1669-1673). The vasodilation is due to the stimulation of muscarinic $M_3$ receptors by acetylcholine and other cholinomimetics on the endothelial cells and the subsequent release of the vasodilator nitric oxide (NO), which is the predominant determinant of resting vascular tone (Brown and Taylor, 2001, Pharmacological Basis of Therapeutics, Hardman, J. G and Limbird, $10^{th}$ edition, pp 155-173; Moody et al., 2001, Pharmacological Basis of Therapeutics, Hardman, J. G and Limbird, $10^{th}$ edition, pp 385-397). When the endothelial cells are injured or damaged, muscarinic receptor-stimulated NO production is reduced. The reduced amount of NO combined with the stimulation of muscarinic receptors in the smooth muscle cells in the presence of unopposed sympathetic adrenergic tone can not only result in loss of vasodilating response but potentially produce a vasoconstriction in blood vessels. Therefore, the vasodilation stimulated by cholinergic agonists is dependent upon a functionally intact endothelium.

Due to the vascular morphologic similarities between humans and rabbits, rabbits have been used as a study model to measure vasomotor responses to drugs. Laher et al. used isolated blood vessels from kidneys or ears of rabbits to demonstrate that α-toxin selectively impairs the endothelium-mediated vasodilation (Laher et al., 1995, Canadian J Physiology Pharmacology 73: 1669-1673). Recently, Drolet et al. (Drolet et al., 2004, Cardiovascular Ultrasound 2:10) uses ultrasound recording of the abdominal aorta to show that the diameter of the abdominal aorta changed from 1 to 4% in response to acetylcholine. These methods either do not provide an appropriate physiologic environment normally present in vivo or lack sufficient dynamic range or sensitivity to examine efficiently the vasomotor response in vivo. Therefore, there is still a need to develop an efficient and sensitive method for measuring vasomotor response in vivo.

The present application provides a method for evaluating the effects of test compounds on vasomotor responses. In addition, a method is provided for evaluating endothelial effects on vasomotor function which is comprised of a systemic exposure to constrictive agents such as norepinephrine, dilatory agents such as acetylcholine, or other agents that augment or interfere with endothelial signaling, and measuring the lumen of the central ear artery of a rabbit. The animal model of arterial vasomotor function of the present application is useful for evaluating the effects of test compounds on basal vascular tone and endothelium-dependent vasomotor function in vivo.

SUMMARY OF THE INVENTION

An object of the present invention is to provide a method of evaluating the effect of a compound on vasomotor response in vivo, which comprises the steps of administering the compound to a rabbit and measuring the diameter of the vessel lumen of a central ear artery of the rabbit in comparison with the baseline diameter of the vessel lumen of the central ear artery of the rabbit. The compound may be a vasodilator or a vasoconstrictor.

Another object of the present invention is to provide a method of evaluating the effect of a compound on vasomotor response in vivo, which comprises the steps of measuring the baseline diameter of the vessel lumen of a central ear artery of a rabbit, administering the compound to the rabbit, then administering a vasoconstrictor to pre-constrict the diameter of the vessel followed by administration of a vasodilator to the rabbit to increase the diameter of the pre-constricted vessel, and determining the effect of the compound on the changes in baseline diameter of the pre-constricted vessel in response to the vasodilator by measuring again the diameter of the vessel lumen of the central ear artery of the rabbit.

Another object of the present invention is to provide a method for evaluating the effect of a compound on vasomotor response in vivo, which comprises the steps of administering the compound to a rabbit, measuring the baseline diameter of the vessel lumen of a central ear artery of the rabbit, then administering a vasoconstrictor to the central ear artery of the rabbit to constrict the diameter of the vessel and determine the effect of the compound on the diameter of the constricted vessel by measuring again the baseline diameter of the vessel lumen of the central ear artery of the rabbit.

Another object of the present invention is to provide a method for evaluating the effect of a compound on vasomotor response in vivo, which comprises the steps of administering the compound to a rabbit, measuring the baseline diameter of the vessel lumen of a central ear artery of the rabbit, and determine the effect of the compound on the diameter of the constricted vessel by measuring again the baseline diameter of the vessel lumen of the central ear artery of the rabbit.

According to the present invention, the compound may be administered to the rabbit orally, peripherally, parenterally or topically and the diameter of said vessel lumen may be measured by an ultrasonic imaging system.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

Figure 1A:
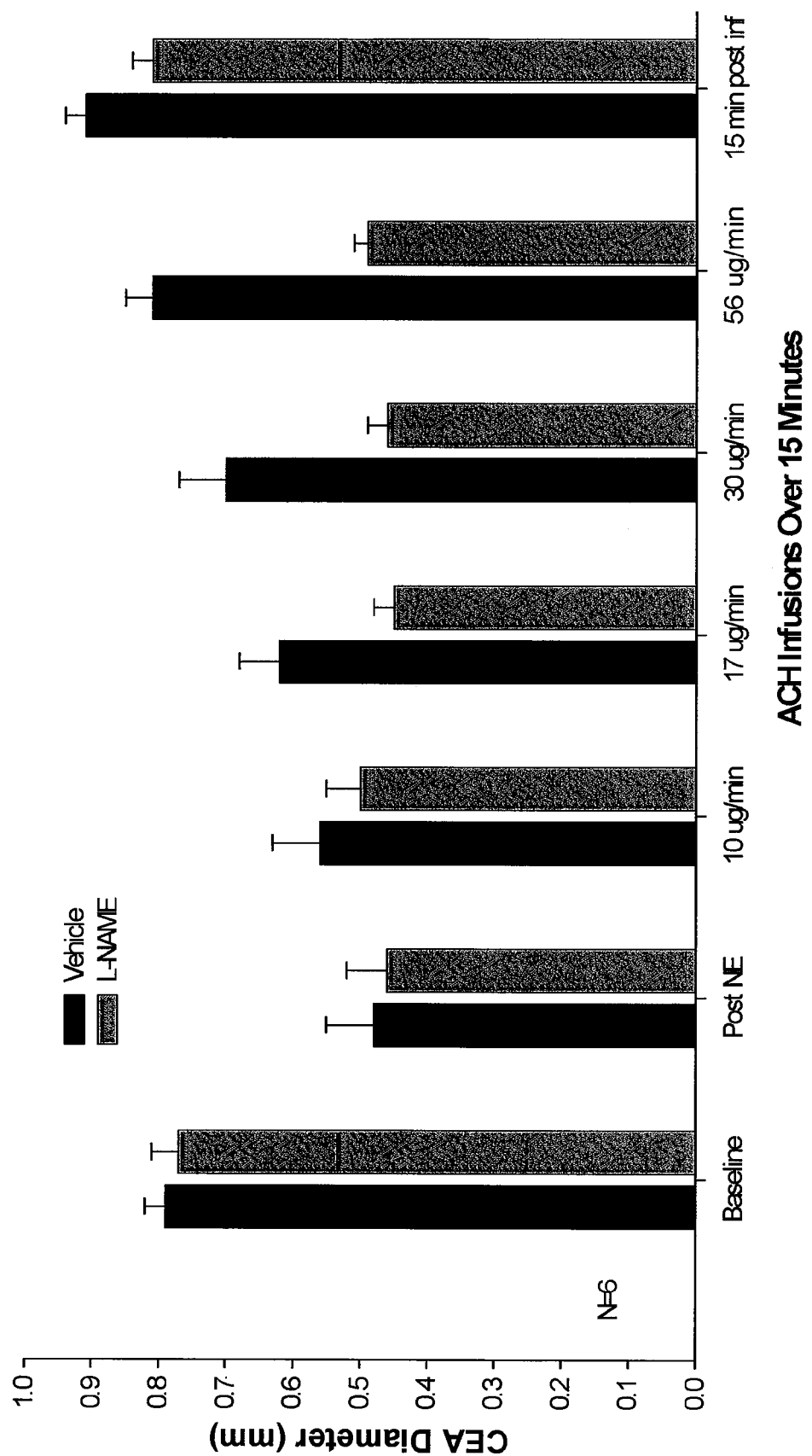
FIG. 1: (A) Effects of L-NAME (N(G)-nitro-L-arginine-methyl ester) on central ear artery lumen diameter in acetylcholine-induced vasodilation in norepinephrine-preconstricted arteries in the rabbit. Data are presented as final mean diameter±SEM. N=6 vessels. (B) Effects of L-NAME on central ear artery lumen area in acetylcholine-induced vasodilation in norepinephrine-preconstricted arteries in the rabbit. Data are presented as final mean area±SEM. N=6.

Abnormalities in vasomotor responses, including endothelium-dependent vasodilation normally mediated by nitric oxide, are thought to play a major role in vascular diseases (CAD, hypertension, etc.) and may be associated with increased cardiovascular risk. Drugs that impair normal vasodilatory mechanisms may increase the risk for adverse cardiovascular events. Clinical studies show higher systolic blood pressure in patients receiving torcetrapib, a cholesteryl ester transfer protein (CETP) inhibitor, (Barter et al., 2007, New England J Med 357:2109-2122). This may be due to the effect of torcetrapib on the vasomotor responses to normal vasodilatory stimuli. As CETP inhibitors are potential drugs for regulating cholesterol metabolism, it is useful to examine CETP inhibitors, including torcetrapib and Compound 2, for their effects on vasomotor responses. Torcetrapib, ethyl (2R, 4S)-4-[[3,5-bis(trifluoromethyl)benzyl](methoxycarbonyl)amino]-2-ethyl-6-(trifluoromethyl)-3,4-dihydroquinoline-1(2H)-carboxylate, has the following chemical structure:

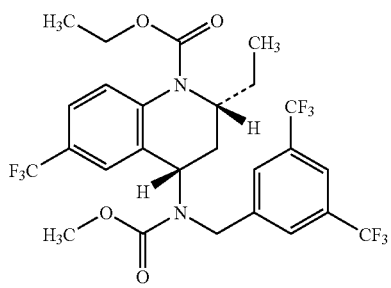 [SMILES: CCOC(=O)N1c2ccc(C(F)(F)F)cc2[C@@H](N(Cc2cc(C(F)(F)F)cc(C(F)(F)F)c2)C(=O)OC)C[C@H]1CC]

Compound 2, 1,1,1-Trifluoro-3-[2-{3-[(1,1,2,2-tetrafluoroethyl)oxy]phenyl}-5-{3-[(trifluoromethyl)oxy]phenyl}-3,4-dihydroquinolin-1(2H)-yl]propan-2-ol, has the following structure:

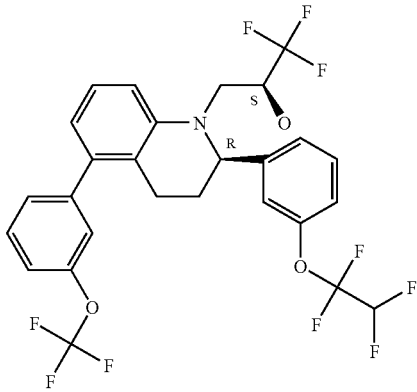

In the present application, a method is provided for evaluating vasomotor responses in vivo. In addition, a method is provided for evaluating effect of a drug or a test compound on vasomotor responses in vivo. The effect of a test compound on vasomotor responses mediated by the endothelium can also be evaluated by inducing vasodilation using cholinergic agonists in a rabbit's central ear artery (CEA) which is pre-constricted with norepinephrine. The test compound may be a dilatory or constrictive agent or have no direct effect on vasomotor tone or vessel diameter, and may include torcetrapib and compound 2.

The terms "dilatory agent", "dilatory drug", "vasodilator" or variations thereof as used herein mean any molecule that is able to increase the diameter of a resistance vessel. By way of examples, the dilatory agent or drug includes, but is not limited to the following compounds: cholinergic agonists such as acetylcholine, methacholine, aceclidine, arecoline, pilocarpine, cevimeline, nitrate compounds (e.g. nitroprusside, nitroglycerin), nitric oxide gas, isoproterenol and related beta-2 adrenoceptor agonists, hydralazine, minoxidil, diazoxide, and other potassium channel openers, verapamil and other calcium channel antagonists, angiotensin converting enzyme (ACE) inhibitors such as captopril, angiotensin receptor antagonists such as losartan, alpha-2 adrenoceptor antagonists including clonidine and others, serotonin antagonists including ketanserin, histamine, ganglionic blocking drugs such as hexamethonium, endothelin receptor antagonists, vasopressin antagonists, phosphodiesterase inhibitors, vasodilatory peptide such as bradykinin and related peptides, adrenomedullin, atrial and brain natriuretic peptides, calcitonin gene-related peptide, and the like.

The terms "constrictive agent", "constrictive drug", "vasoconstrictor" or variations thereof as used herein mean any molecule that is able to decrease the diameter of a resistance vessel. By way of examples, the constrictive agent includes, but is not limited to the following compounds: norepinephrine, epinephrine, phenylephrine, methoxamine, mephentermine, metaraminol, midodrine, high-dose dopamine, cocaine, amphetamine and related agents, serotonin, vasopressin and related analogs, angiotensin II and related peptides, endothelin peptides, urotensin II, and the like.

To examine the vasomotor responses in the presence of a vasodilator or vasoconstrictor in vivo, the central artery of a rabbit ear was exposed to these agents. It is found herein that the CEA, a resistance vessel, is able to undergo large changes in the diameter of the vessel lumen in response to a vasodilator or vasoconstrictor. This is in contrast to the use of the aorta or other elastic artery, which undergoes minimal changes in the diameter of the vessel lumen in response to these agents.

A group of six rabbits was anesthetized with a mixture of ketamine (50 mg/kg)/xylazine (100 mg/kg) administered intramuscularly and placed on a warming pad to maintain body temperature. Rabbit ear pinnae were shaved and depilitated using an over-the-counter depilatory agent. A segment of about 2 cm of the dorsal surface over the CEA on the right ear was coated with warmed ultrasonic gel. The baseline diameter and area of the rabbit's CEA were evaluated using a 23.5 MHz ultrasonic probe (model RMV 708). The images were recorded on a VISUALSONICS VEVO 600 system where the CEA lumen diameters and areas were subsequently measured. The vessel lumen diameter and area were expressed as mean and standard error of the mean (SEM). Norepinephrine and acetylcholine were infused in the contralateral left ear vein through a 27-gauge butterfly needle infusion set connected to an infusion pump. Images were obtained at about 5 minute intervals throughout the infusion periods.

To confirm that acetylcholine-induced vasodilation was NO-dependent, a second group of six rabbits was dosed with either the nitric oxide synthase inhibitor L-NAME (400 µg/mL) mixed in TANG® flavored drinking water (N=3) or TANG® flavored drinking water alone (N=3) for 5 consecutive days. L-NAME, N(G)-nitro-L-arginine-methyl ester, is an arginine derivative that blocks normal nitric oxide-dependent vasodilation. The rabbit CEA were then imaged on day 6. The rabbits were allowed to recover for about one week and then in crossover fashion each group of 3 was given the opposite treatment for 5 days and then imaged on day 6.

In another group, six adult New Zealand male rabbits (2.5-3.5 kg) were dosed orally (gavage with feeding tube) with the Imwitor/Cremophor/Water vehicle for 4 consecutive days during week 1. The vehicle (10% Imwitor, 20% Cremophor RH40 and 70% water, a light milky compound solution) was given in a total volume of 3 mL/kg per day. On day 4, three hours after oral dosing with vehicle or drug, the rabbits were anesthetized and measured for the vehicle's effect on CEA vessel lumen as described above. After week 1, the rabbits were allowed to recover for 3 days and were then orally dosed with a test compound such as torcetrapib or compound 2 at about 30 mg/kg for 4 consecutive days during week 2. On the $4^{th}$ day of week 2, rabbit CEA diameter changes in response to test compounds were assessed with infusion of norepinephrine followed by acetylcholine as described above. Rabbits were again allowed to recover for an additional week to allow for drug elimination and were then subjected to daily vehicle dosing and CEA diameter changes in response to test compounds were assessed as described above.

The test compound may be administered either orally, peripherally, parenterally, or topically. The amount of each administration of the test compound and the duration of treatment may vary, depending on the potency or the nature of the test compound, which can be readily determined by a person skilled in the art.

The present rabbit CEA model is shown to be sensitive to norepinephrine which induces vasoconstriction and acetylcholine which induces vasodilation in the context of norepinephrine-induced preconstriction. Also, the effect of acetylcholine is shown to be nitric oxide-dependent as shown by the lack of, vasodilation in response to acetylcholine infusion in the group receiving L-NAME pretreatment. Daily administration of torcetrapib causes an increase in basal vasoconstrictor tone and abolishes the acetylcholine-induced vasodilation compared to vehicle treatment. Compound 2 has no effect on basal vascular tone or the acetylcholine-induced vasodilation.

One skilled in the art will know other suitable variations or modifications to the method described herein, and will be able to adapt such method for the use of a rabbit's CEA according to the present application. For example, the CEA of a diseased rabbit may be used for evaluating the effect of a test compound on vasomotor responses in a pathologic condition. Blood vessels in the diseased rabbit may exhibit abnormal baseline vasomotor tone and/or may respond abnormally to constrictive or dilatory stimuli due to the pathology. This may facilitate the understanding of vasomotor responses mediated by the endothelium under some pathologic conditions. Further, the CEA of the diseased rabbit may not need to be pretreated with a vasodilator or vasoconstrictor. The effect of a test compound on vasomotor responses may be evaluated by assessing the effects of the compound on baseline diameter or area of CEA vessel lumen. This is useful in identifying a drug or compound which is able to constrict or dilate the diseased vessels directly, and is useful in understanding the pathophysiologic impact of disease on the vessel or treating the vascular effects of the disease. In addition, CEA of normal and diseased rabbits may be used for a head-to-head comparison to understand the effects of a test compound.

Example 1

Evaluating Vasomotor Response Induced by Acetylcholine and Norepinephrine

A series of 5 images (approximately 5 minutes apart) of the CEA were taken and used for baseline lumen diameter (mm) and area ($mm^2$) measurements, respectively. The adrenergic agonist norepinephrine was slowly infused at about 28 µg per minute and maintained for the duration of the procedure. An infusion of acetylcholine was administered in escalating doses at about 10, 17, 30 and 56 μg/min, each for 15 minutes, in conjunction with the infusion of norepinephrine. The images were collected several times during each infusion period of 15 minutes. After the final acetylcholine and concurrent norepinephrine infusion period, all infusions were terminated and the vessel was allowed to return to its original size. About two mL of blood were sampled from the non-imaged contralateral CEA immediately after the last measurement. All samples were collected into tubes containing EDTA and centrifuged at about 10,000 rpm for 6 minutes. Plasma was kept in −80° C. until analyzed for the concentration of the tested compounds. In addition, blood was taken from a naïve rabbit for generation of a standard drug concentration curve.

In anesthetized rabbits without any treatment of a dilatory agent, a constrictive agent, or a test compound, the baseline CEA lumen diameter and area were found to be about 0.8-0.9 mm and about 0.6-0.7 $mm^2$, respectively. The baseline CEA lumen diameter was unaffected by intravenous saline infusion. As used herein, the phrase baseline CEA lumen diameter and area or the variant refers to the first measurement of the vascular caliber of CEA lumen prior to the administration of any compound.

In the group which received acetylcholine infusion alone, the baseline CEA diameter and area was not changed in the anesthetized rabbit at doses up to 56 μg/min. This showed that acetylcholine had no effect on the already dilated lumen.

In the group in which norepinephrine was infused, the CEA lumen diameter and area were reduced to about 0.5 mm and about 0.2 $mm^2$, respectively. The subsequent infusion of acetylcholine in the rabbits with preconstricted CEA restored the vessel lumen to the baseline diameter and area. These results showed that the rabbit CEA model provides for assessment of vasomotor changes in the range of about 44 or 70% of the baseline diameter or lumen area, respectively.

Figure 1B:
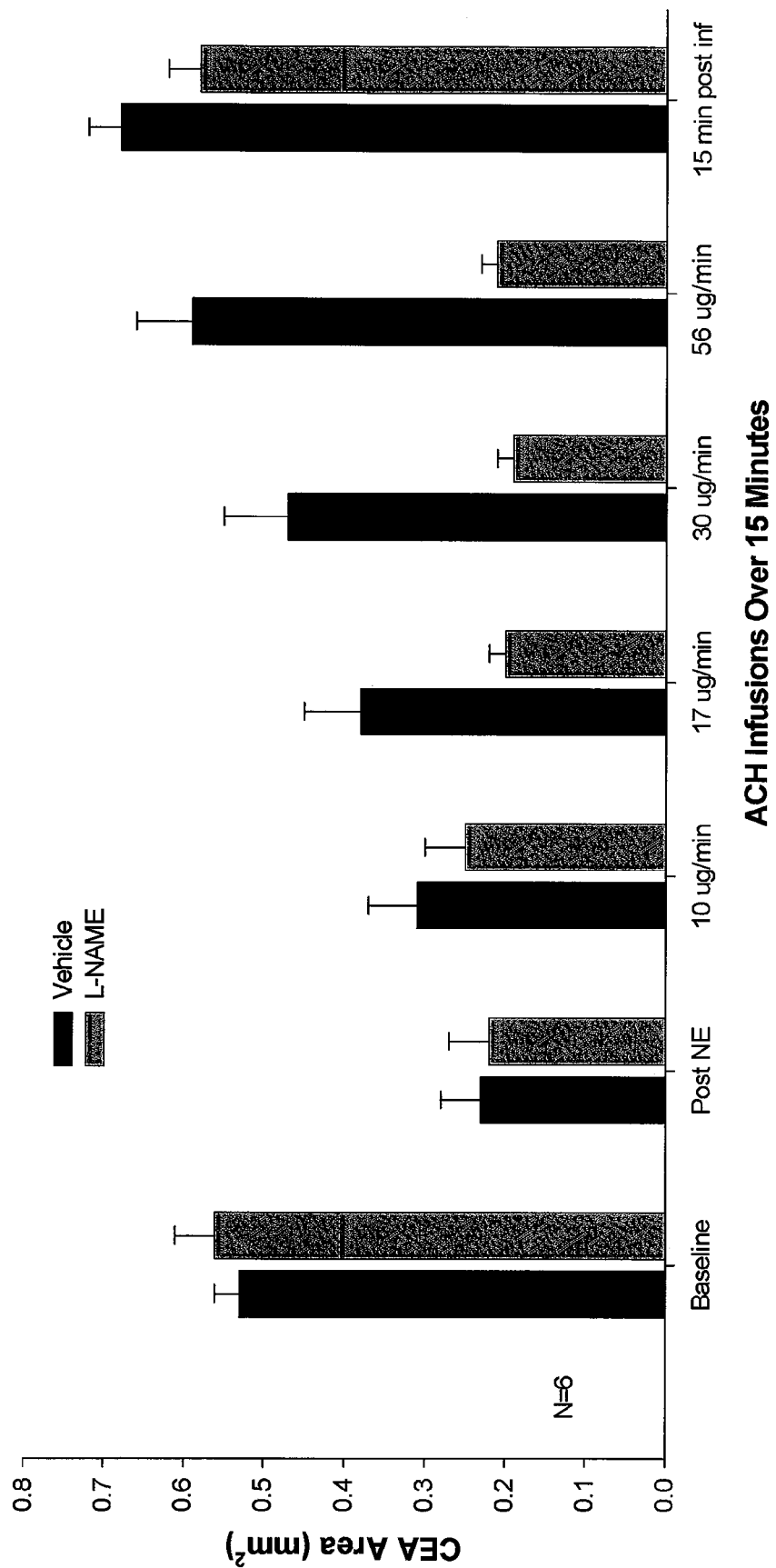

To examine whether these responses were mediated by nitric oxide, a nitric oxide synthase inhibitor, L-NAME, was administered in drinking water (400 μg/mL) to the rabbits treated with acetylcholine and norepinephrine. The results of Example 1 show that the acetylcholine-induced vasodilation in the norepinephrine-preconstricted CEA is dose-dependent, and that the treatment with L-NAME inhibits this acetylcholine-induced vasodilation (FIGS. 1A and 1B). This indicates that the vasodilation response of the pre-constricted CEA is mediated NO and that the rabbit CEA models the endothelial function in vivo.

Example 2

Evaluating the Effects of Test Compounds on Vasodilatory Response

The effects of torcetrapib and compound 2 on vasomotor tone were examined by orally dosing the rabbits with vehicle for 4 days followed by oral dosing of these compounds. The CEA vessel lumen of the treated rabbits were measured as described above.

Figure 2A:
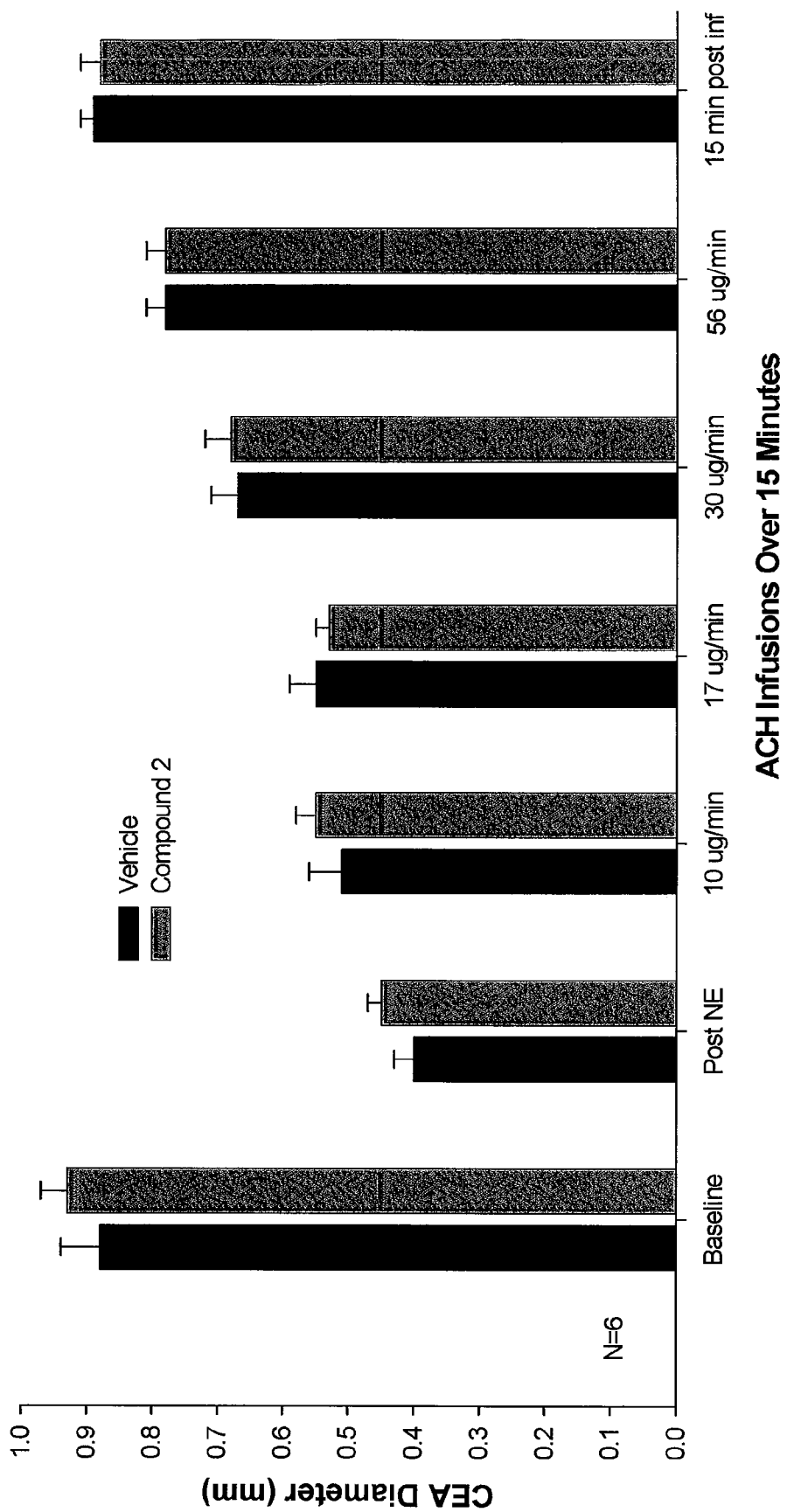
FIG. 2: (A) Effect of compound 2 on central ear artery lumen diameter in acetylcholine-induced vasodilation in norepinephrine-preconstricted arteries in the rabbit. Data are presented as final mean diameter±SEM. N=6. (B) Effect of compound 2 on central ear artery lumen area in acetylcholine-induced vasodilation in norepinephrine pre-constricted arteries in the rabbit. Data are presented as final mean area±SEM. N=6.
Figure 2B:
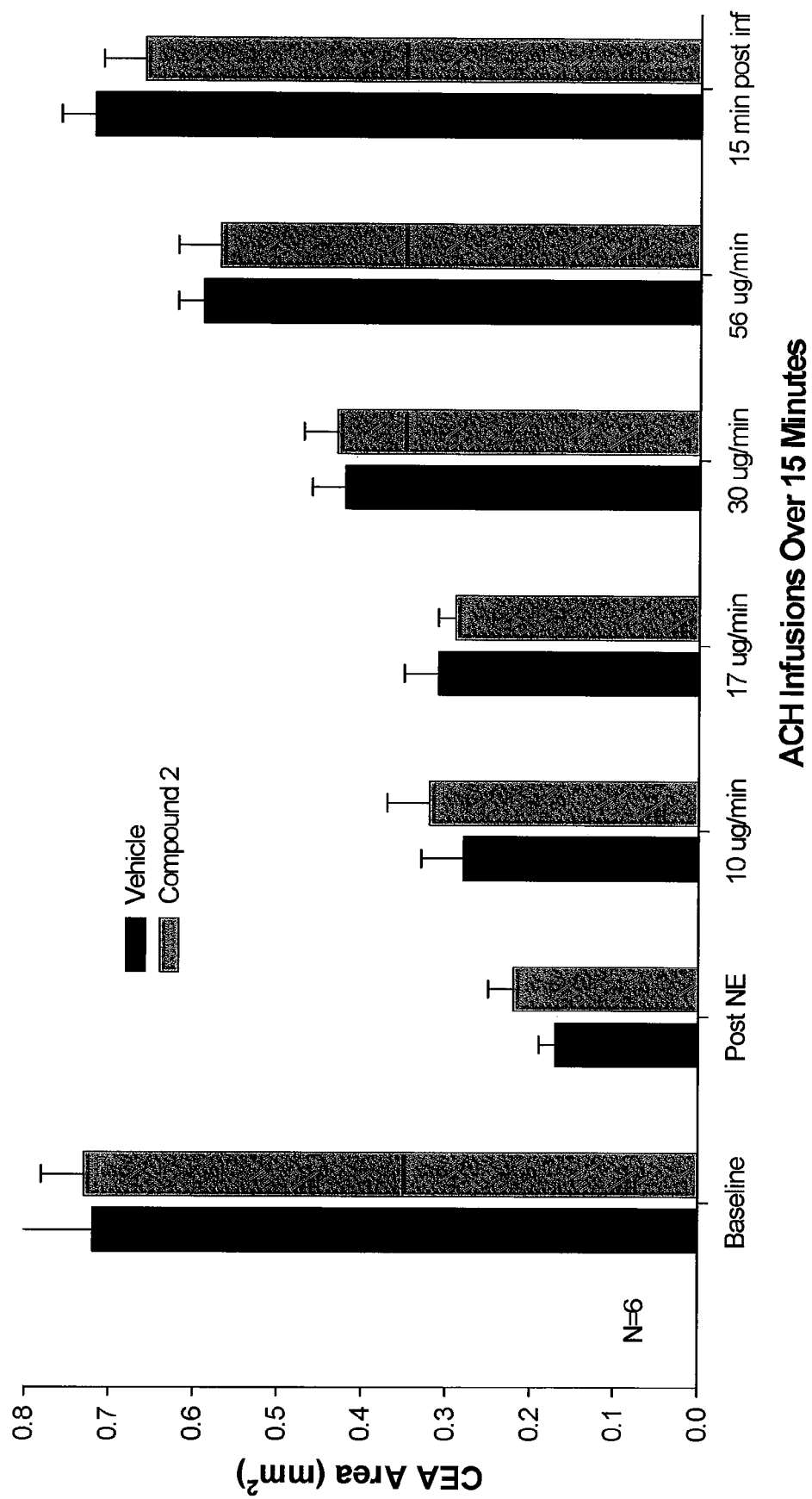

In the rabbits treated with compound 2 at an oral dose of about 30 mg/kg for 4 days, the baseline CEA lumen diameter and area in the treated rabbits were similar to those of vehicle (FIGS. 2A and B). As shown in FIG. 2, the vehicle had no effect on the acetylcholine-induced vasodilation in norepinephrine-preconstricted CEA lumen diameter and area. After administering norepinephrine and acetylcholine, the CEA lumen diameter and area in the compound 2-treated rabbits were about 0.8 mm and 0.6 $mm^2$, respectively, similar to those of the vehicle group (FIGS. 2A and 2B). Four hours after the last oral dosing, the blood samples were collected to determine the concentration of the compound 2 in the rabbits. The plasma concentration in the rabbits treated with compound 2 are 2.58±0.67 μM at 4 hours after the last dose. This indicates that compound 2 does not affect the baseline CEA lumen diameter and area or the acetylcholine-induced vasodilation in norepinephrine-preconstricted CEA vessel lumen and area despite its abundance in plasma.

Figure 3A:
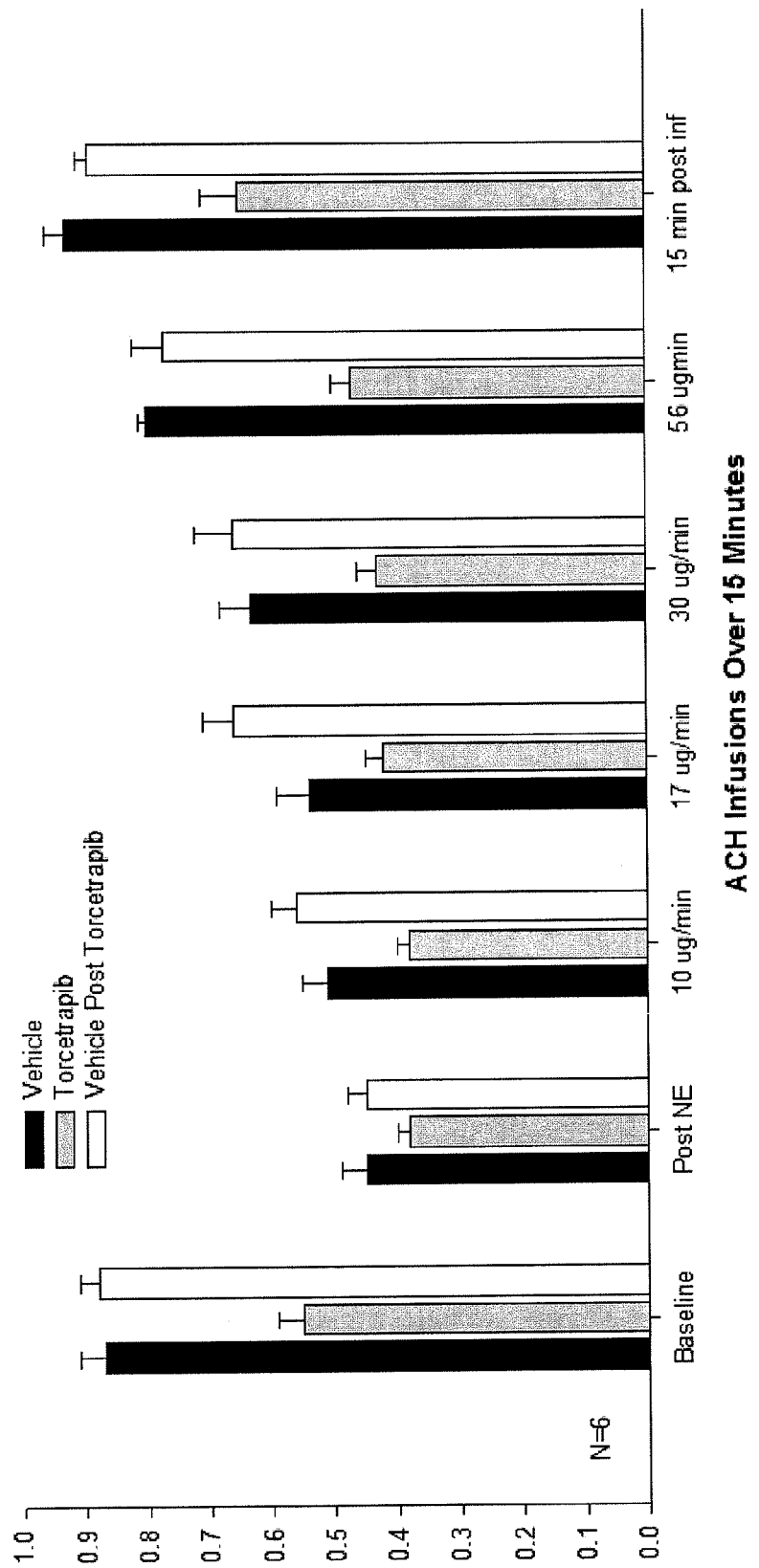
FIG. 3: (A) Effect of torcetrapib on central ear artery lumen diameter in acetylcholine-induced vasodilation in norepinephrine-preconstricted arteries in the rabbit. Data are presented as final mean diameter±SEM. N=6. (B) Effect of torcetrapib on central ear artery lumen area in acetylcholine-induced vasodilation in norepinephrine-preconstricted arteries in the rabbit. Data are presented as final mean area±SEM. N=6.
Figure 3B:
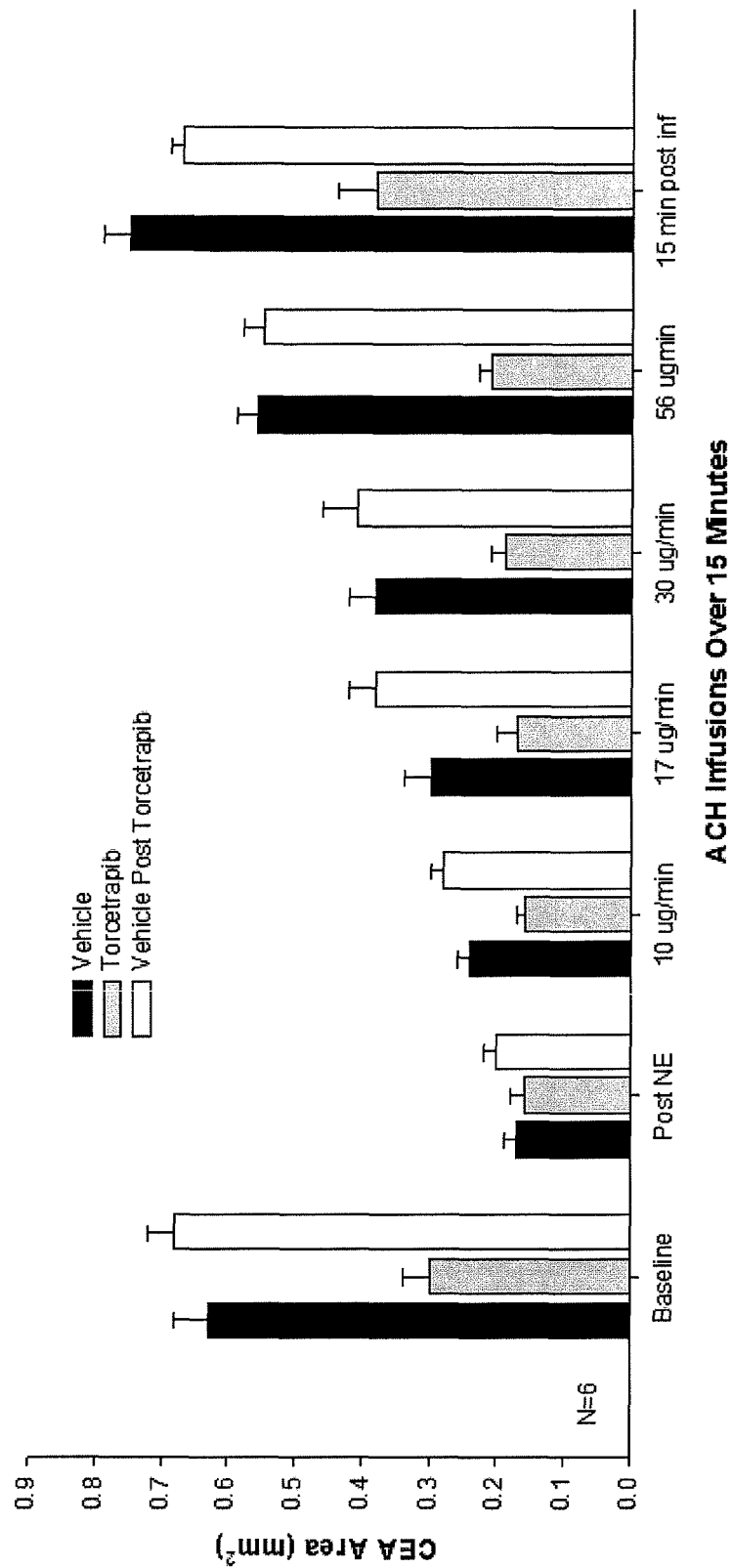

In the rabbits administered torcetrapib at an oral dose of 30 mg/kg for 4 days prior to administering norepinephrine or acetylcholine, the baseline CEA lumen diameter was reduced to about 0.55 mm compared to 0.85 mm in the vehicle group, and the baseline CEA lumen area was reduced to about 0.3 $mm^2$ compared to 0.65 $mm^2$ in the vehicle group (FIGS. 3A and 3B). After administering norepinephrine, the acetylcholine-induced vasodilation response in torcetrapib-treated rabbits as measured by CEA vessel lumen diameter and area was reduced to about 0.45 mm compared to 0.8 mm in the vehicle group. (Corresponding changes in CEA lumen area were 0.2 $mm^2$ compared to 0.6 $mm^2$ in the vehicle group). The plasma concentration in the rabbits treated with torcetrapib was about 1.01±0.54 μM at 4 hours after the last dose. This indicates that torcetrapib caused a measurable baseline vasoconstriction and that torcetrapib inhibits the acetylcholine-induced vasodilation in norepinephrine-preconstricted CEA vessel lumen with its levels in plasma being lower than compound 2.

In Example 2, the results show that once daily oral administration of torcetrapib (30 mg/kg) for four days produced basal vasoconstriction and inhibition of acetylcholine-induced dilation of norepinephrine-preconstricted central ear artery of anesthetized rabbits when compared to vehicle-treated controls. Compound 2 administered orally at the same dose with the same regimen produces no basal vasoconstriction and no effect on acetylcholine-induced vasodilation following norepinephrine-preconstriction. Plasma levels sampled 4 hours after the last dose of either compound indicates that each drug was present in micromolar concentrations and that the plasma concentration of compound 2 exceeded that of torcetrapib by approximately 2.5-fold. The differential responses of these two compounds indicated that not all CETP inhibitors interfere with baseline and endothelial-dependent vasomotor responses.

Thus, while there have been shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

We claim:
1. A method for evaluating the effect of a compound on vasomotor response in vivo, comprising the steps of:
   a. measuring the baseline diameter of the vessel lumen of a central ear artery (CEA) of a rabbit;
   b. administering said compound to said rabbit;

c. administering a vasoconstrictor to said CEA of said rabbit to pre-constrict the diameter of said vessel after administration of said compound;

d. administering a vasodilator to said CEA of said rabbit to increase the diameter of said pre-constricted vessel after administration of said vasoconstrictor; and e. determining the effect of said compound on the diameter of said vessel lumen resulting from steps c and d by measuring the diameter of said vessel lumen of said CEA of said rabbit and comparing said diameter to the baseline diameter of said vessel lumen which is measured in step a, wherein the baseline diameter of said vessel lumen measured in step a and the diameter of said vessel lumen measured in step e are measured noninvasively.

2. The method of claim 1, wherein the baseline diameter of said vessel lumen measured in step a and the diameter of said vessel lumen measured in step e are measured by an ultrasonic imaging system.

3. The method of claim 1, wherein said vasoconstrictor is selected from the group consisting of norepinephrine, epinephrine, phenylephrine, methoxamine, mephentermine, metaraminol, midodrine, high-dose dopamine, cocaine, amphetamine, serotonin, vasopressin, angiotensin II, endothelin peptides, urotensin II, and combinations thereof.

4. The method of claim 1, wherein said vasodilator is selected from the group consisting of acetylcholine, methacholine, aceclidine, arecoline, pilocarpine, cevimeline, nitroprusside, nitroglycerin, hydralazine, minoxidil, diazoxide, verapamil, calcium channel antagonists, captopril, losartan, clonidine, ketanserin, histamine, hexamethonium, bradykinin, adrenomedullin, atrial natriuretic peptides, brain natriuretic peptides, calcitonin gene-related peptide, and combinations thereof.

5. The method of claim 1, wherein said vasodilator is a cholinergic agonist or a vasodilator peptide.

6. The method of claim 5, wherein said vasodilator is a cholinergic agonist selected from the group consisting of acetylcholine, methacholine, aceclidine, arecoline, pilocarpine, cevimeline, and combinations thereof.

7. The method of claim 5, wherein said vasodilator is a vasodilator peptide selected from the group consisting of bradykinin, adrenomedullin, atrial natriuretic peptides, brain natriuretic peptides, calcitonin gene-related peptide, and combinations.

8. A method of identifying compounds that interfere with endothelium-mediated vasodilation comprising:
   a. measuring the baseline diameter of the vessel lumen of a central ear artery (CEA) of a rabbit;
   b. obtaining a compound to be tested;
   c. administering said compound to said rabbit;
   d. administering a vasoconstrictor to said CEA of said rabbit to pre-constrict the diameter of said vessel after administration of said compound;
   e. administering a vasodilator to said CEA of said rabbit to increase the diameter of said pre-constricted vessel after administration of said vasoconstrictor;
   f. measuring the diameter of the vessel lumen of said CEA of said rabbit after steps d and e;
   g. comparing the diameter of the vessel lumen measured in step f to the baseline diameter of the vessel lumen measured in step a to determine whether the test compound had an effect on the activity of the vasodilator; and
   h. identifying whether said compound interferes with endothelium-mediated vasodilation, wherein the baseline diameter of said vessel lumen measured in step a and the diameter of said vessel lumen measured in step f are measured noninvasively.

9. The method of claim 8, wherein the baseline diameter of said vessel lumen measured in step a and the diameter of said vessel lumen measured in step f are measured by an ultrasonic imaging system.

10. The method of claim 8, wherein said vasoconstrictor is selected from the group consisting of norepinephrine, epinephrine, phenylephrine, methoxamine, mephentermine, metaraminol, midodrine, high-dose dopamine, cocaine, amphetamine, serotonin, vasopressin, angiotensin II, endothelin peptides, urotensin II, and combinations thereof.

11. The method of claim 8, wherein said vasodilator is selected from the group consisting of acetylcholine, methacholine, aceclidine, arecoline, pilocarpine, cevimeline, nitroprusside, nitroglycerin, hydralazine, minoxidil, diazoxide, verapamil, calcium channel antagonists, captopril, losartan, clonidine, ketanserin, histamine, hexamethonium, bradykinin, adrenomedullin, atrial natriuretic peptides, brain natriuretic peptides, calcitonin gene-related peptide, and combinations thereof.

12. The method of claim 8, wherein said vasodilator is a cholinergic agonist or a vasodilator peptide.

13. The method of claim 12, wherein said vasodilator is a cholinergic agonist selected from the group consisting of acetylcholine, methacholine, aceclidine, arecoline, pilocarpine, cevimeline, and combinations thereof.

14. The method of claim 12, wherein said vasodilator is a vasodilator peptide selected from the group consisting of bradykinin, adrenomedullin, atrial natriuretic peptides, brain natriuretic peptides, calcitonin gene-related peptide, and combinations thereof.

15. The method of claim 8, wherein said vasoconstrictor is norepinephrine.

* * * * *